United States Patent
McCort et al.

[11] Patent Number: 5,958,924
[45] Date of Patent: Sep. 28, 1999

[54] QUINOLEIN-2 (1H)-ONE DERIVATIVES AS SEROTONIN ANTAGONISTS

[75] Inventors: Gary McCort, Paris; Christian Hoornaert, Antony; Geneviéve Dellac, Morangis; Michel Aletru, Paris, all of France

[73] Assignee: SYNTHELABO, Le Plessis Robinson, France

[21] Appl. No.: 09/011,482

[22] PCT Filed: Sep. 12, 1996

[86] PCT No.: PCT/FR96/01401

§ 371 Date: Feb. 4, 1998

§ 102(e) Date: Feb. 4, 1998

[87] PCT Pub. No.: WO97/10238

PCT Pub. Date: Mar. 20, 1997

[30] Foreign Application Priority Data

Sep. 15, 1995 [FR] France ................... 95 10815
Sep. 21, 1995 [FR] France ................... 95 11083

[51] Int. Cl.⁶ .............. C07D 401/06; C07D 495/04; A61K 31/47
[52] U.S. Cl. .............. 514/252; 544/383; 546/158; 514/312
[58] Field of Search .............. 546/114, 158, 546/312, 383

[56] References Cited

U.S. PATENT DOCUMENTS 5,077,288 12/1991 Lavielle et al. ................ 514/210

FOREIGN PATENT DOCUMENTS 0 288 563  11/1988  European Pat. Off. .
2174703    11/1986  United Kingdom .
9710238    3/1997   WIPO .

OTHER PUBLICATIONS

Journal of Medicinal Chemistry, vol. 35, No. 26, Dec. 25, 1992 pp. 4903–4910.
Journal of Medicinal Chemistry, vol. 32, No. 6, Jun. 1989, pp. 1147–1156.

Primary Examiner—Richard L. Raymond
Assistant Examiner—Ann Razgunas
Attorney, Agent, or Firm—Jacobson, Price, Holman & Stern, PLLC

[57] ABSTRACT

Compounds of formula (I)

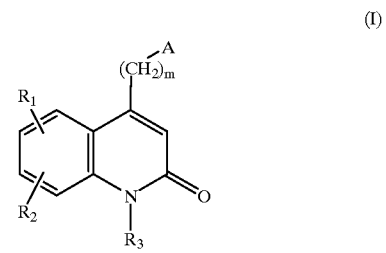

in which A represents a 4-(thieno[3,2-c] pyridin-4-yl)-1-piperazinyl or 4-(4-fluorobenzoyl)-1-piperidyl group, $R_1$ and $R_2$ each represent, independently of one another, either a hydrogen or halogen atom, or an amino, hydroxyl, nitro, cyano, $(C_1$–$C_6)$alkyl, $(C_1$–$C_6)$alkoxy, trifluoromethyl, trifluoromethoxy or —COOH group, a group —COOR$_4$, a —CONH$_2$ group or a group —CONHR$_4$, —CONR$_4$R$_5$, —SR$_4$, —SO$_2$R$_4$, —NHCOR$_4$, —NHS0$_2$R$_4$ or —N(R$_4$)$_2$, where $R_4$ and $R_5$ are each a $(C_1$–$C_4)$alkyl group, $R_3$ represents either a hydrogen atom, or a $(C_1$–$C_4)$alkyl group, or a group —(CH$_2$)OH, —(CH$_2$)$_p$NH$_2$, —(CH$_2$)$_n$COOH, —(CH$_2$)$_n$COOR$_4$, —(CH$_2$)$_n$CONH$_2$, —(CH$_2$)$_n$CONHOH, —(CH$_2$)$_p$SH, —(CH$_2$)$_n$SO$_3$H, —(CH$_2$)$_n$SO$_2$NH$_2$, —(CH$_2$)$_n$SO$_2$NHR$_4$, —(CH$_2$)$_n$SO$_2$NH$_4$R$_5$, —(CH$_2$)$_n$CONHR$_4$, —(CH$_2$)$_n$CONR$_4$R$_5$, —(CH$_2$)$_p$NHSO$_2$R$_4$, —(CH$_2$)$_p$NHCOR$_4$ or —(CH$_2$)$_p$OCOR$_4$, where $R_4$ and $R_5$ are each a $(C_1$–$C_4)$alkyl group, n is equal to 1, 2, 3 or 4, p is equal to 2, 3 or 4 and m is equal to 2, 3 or 4. use in therapy.

9 Claims, No Drawings

QUINOLEIN-2 (1H)-ONE DERIVATIVES AS SEROTONIN ANTAGONISTS

This application is a 371 of PCT//FR96/01401 filed Sep. 12, 1996.

The present invention relates to 2(1H)-quinolone derivatives, to their preparation and to their use in therapy.

The compounds of the invention correspond to the formula (I)

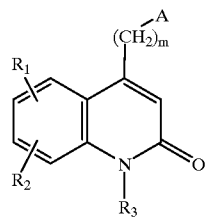

(I)

in which

A represents either a 4- (thieno[3,2-c]pyridin-4-yl)-1-piperazinyl group or a 4-(4-fluorobenzoyl)-1-piperidyl group, $R_1$ and $R_2$ each represent, independently of one another, either a hydrogen atom, or a halogen atom, or an amino group, or a hydroxyl group, or a nitro group, or a cyano group, or a ($C_1$–$C_6$)alkyl group, or a ($C_1$–$C_6$)alkoxy group, or a trifluoromethyl group, or a trifluoromethoxy group, or a —COOH group, or a group —COOR$_4$, or a —CONH$_2$ group, or a group —CONHR$_4$, or a group —CONR$_4$R$_5$, or a group —SR$_4$, or a group —SO$_2$R$_4$, or a group —NHCOR$_4$, or a group —NHSO$_2$R$_4$, or a group —N(R$_4$)$_2$, where R$_4$ and R$_5$ are each a ($C_1$–$C_4$) alkyl group, R$_3$ represents either a hydrogen atom, or a ($C_1$–$C_4$)alkyl group, or a group —(CH$_2$)$_p$OH, or a group —(CH$_2$)$_p$NH$_2$, or a group —(CH$_2$)$_n$COOH, or a group —(CH$_2$) COOR$_4$, or a group —(CH$_2$)$_n$CONH$_2$, or a group —(CH$_2$)$_n$CONHOH, or a group —(CH$_2$)$_p$SH, or a group —(CH$_2$)$_n$SO$_3$H, or a group —(CH$_2$)$_n$SO$_2$NH$_2$, or a group —(CH$_2$)$_n$SO$_2$NHR$_4$, or a group —(CH$_2$)$_n$SO$_2$NR$_4$R$_5$, or a group —(CH$_2$)$_n$CONHR$_4$, or a group —(CH$_2$)$_n$CONR$_4$R$_5$, or a group —(CH$_2$)$_p$NHSO$_2$R$_4$, or a group —(CH$_2$)$_p$NHCOR$_4$, or a group —(CH$_2$)$_p$OCOR$_4$, where R$_4$ and R$_5$ are each a ($C_1$–$C_4$) alkyl group, n is equal to 1, 2, 3 or 4, p is equal to 2, 3 or 4 and m is equal to 2, 3 or 4 as well as their addition salts with pharmaceutically acceptable acids or bases.

According to the invention, the compounds of formula (I) may be synthesized according to Scheme 1.

4-(Acetyloxy)-2H,3H-pyran-2,6-dione is reacted with a compound of formula (II) (in which $R_1$ and $R_2$ are as defined above and $R_3$ is a hydrogen atom or a ($C_1$–$C_4$)alkyl group) at room temperature in a polar solvent such as acetic acid. After drying, the compound of formula (III) thereby obtained is cyclized in the presence of an inorganic or organic acid, preferably anhydrous, such as concentrated sulphuric acid, polyphosphoric acid or trifluoromethanesulphonic acid, at a temperature of between 10 and 150° C., and a substituted or unsubstituted 2-oxo-1,2-dihydro-4-quinolineacetic acid of formula (IV) is obtained, which is esterified with an alcohol of formula R$_6$OH (where R$_6$ is a ($C_1$–$C_4$)alkyl group) by any esterification method,

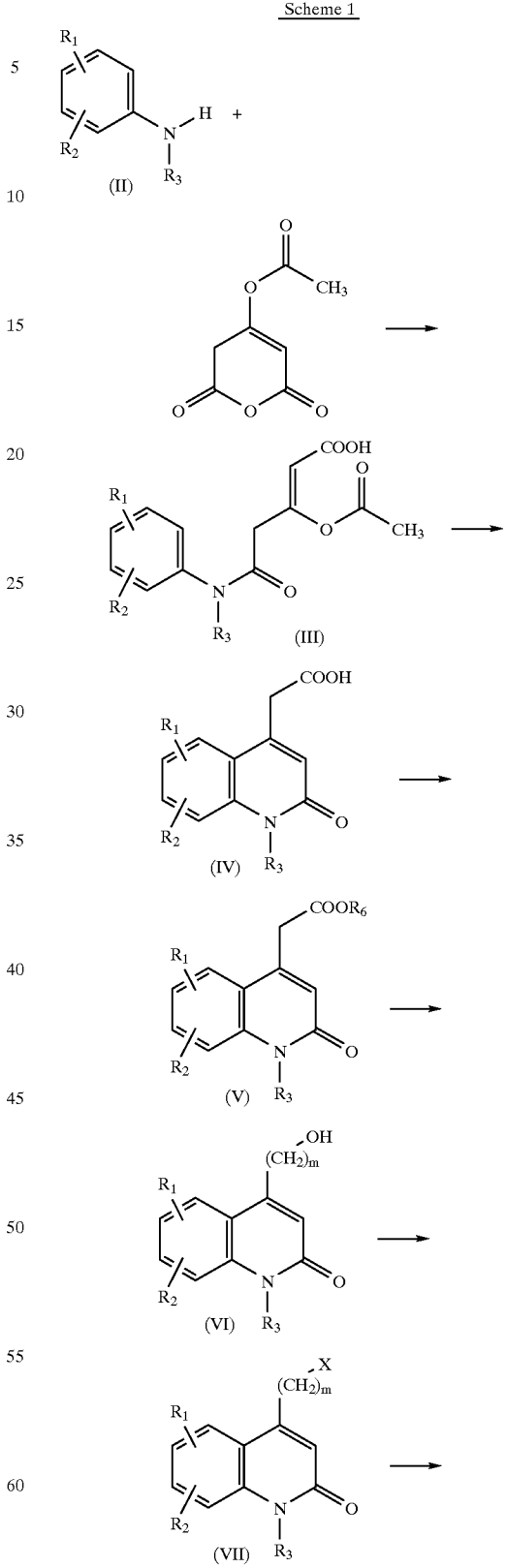

Scheme 1

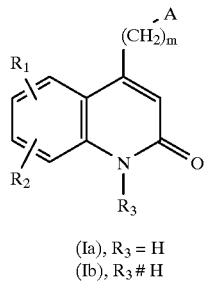

(Ia), R$_3$ = H
(Ib), R$_3$ ≠ H preferably by the action of thionyl chloride. The ester of formula (V) thereby obtained is then reduced with a hydride in an aprotic solvent such as, for example, lithium aluminium hydride in dioxane or sodium borohydride in excess in tetrahydrofuran under reflux, or lithium borohydride in tetrahydrofuran at room temperature, to obtain an alcohol of formula (VI) (in which m is equal to 2); the compounds of formula (VI) in which m is equal to 3 or 4 are obtained from those in which m is equal to 2 by homologation techniques known to a person skilled in the art. The compounds of formula (VI) (in which m is equal to 2, 3 or 4) are then activated to compounds of formula (VII) (in which X represents a leaving group such as a chlorine or bromine atom), for example by reaction with thionyl chloride in chloroform under reflux or dibromotriphenylphosphorane at room temperature in dichloromethane, or to compounds of formula (VII) (in which X represents a leaving group such as methanesulphonyloxy, trifluoromethanesulphonyloxy or para-toluenesulphonyloxy groups), for example by reaction with a sulphonic anhydride or a sulphonic acid chloride in the presence of a base such as pyridine or triethylamine. Finally, the compounds of formula (VII) are reacted with 4-(1-piperazinyl)thieno[3,2-c]pyridine or with 4-(4-fluorobenzoyl)piperidine with or without an aprotic or protic solvent, in the presence of an inorganic base, at between 20 and 150° C., preferably in acetonitrile or dimethylformamide in contact with sodium bicarbonate, and a compound of formula (I) is obtained.

To prepare a compound of formula (Ib) (in which R$_3$ is other than a hydrogen atom), alkylation of the corresponding compound of formula (Ia) (in which R$_3$ represents a hydrogen atom) may be carried out using an electrophilic agent of the type R$_3$Br or R$_3$I, such as, for example, tert-butyl bromoacetate, bromomethanesulphonamide, N-methylbromomethanesulphonamide, bromoacetamide, N-methylbromoacetamide, N,N-dimethylbromoacetamide or 2-bromoethyl acetate, in the presence of a base such as sodium hydride or potassium hydride, in an aprotic solvent such as tetrahydrofuran or dimethylformamide, in the presence or otherwise of a phase transfer catalyst such as tetrabutylammonium bromide. Then, if it is desired to prepare the compounds of formula (Ib) in which R$_3$ represents a group —(CH$_2$)$_n$COOH, a de-esterification of the corresponding compounds of formula (Ib) in which R$_3$ represents a group —(CH$_2$)$_n$COOR$_4$ is carried out. If it is desired to prepare the compounds of formula (Ib) in which R$_3$ represents a group —(CH$_2$)$_p$OH, a de-acetylation of the corresponding compounds of formula (Ib) in which R$_3$ represents a group —(CH$_2$)$_p$OCOR$_4$ is carried out.

To obtain a compound of formula (I) in which R$_1$ and/or R$_2$ represent(s) a cyano, —CONH$_2$, or —COOH group or a group —COOR$_4$, —SR$_4$ or —SO$_2$R$_4$ where R$_4$ is a (C$_1$–C$_4$) alkyl group, the cyclization of the compound of formula (III) to the quinolone of formula (IV) being disfavored, the synthesis of the corresponding compounds of formulae (V) and (VI) is conducted instead according to Schemes 2 and 3.

According to Scheme 2, a compound of formula (Va), corresponding to a compound of formula (V) (in which R$_1$ represents an iodine atom, R$_2$ and R$_6$ are as defined above and R$_3$ is a hydrogen atom or a (C$_1$–C$_4$)alkyl group), is reacted with a cyanide salt in the presence of a copper salt in a polar solvent such as dimethylformamide or N-methylpyrrolidone, or with trimethylsilyl cyanide in the presence of a palladium catalyst, preferably tetrakis (triphenylphosphine)palladium[0] in triethylamine under reflux, to obtain a compound of formula (Vb), which may be either converted to a compound of formula (VId) and then to a compound of formula (VIe) (in which R$_7$ is a hydrogen atom or a (C$_1$–C$_4$)alkyl group), or converted to a carboxamide derivative of formula (Vc) by standard methods known to a person skilled in the art.

Scheme 2

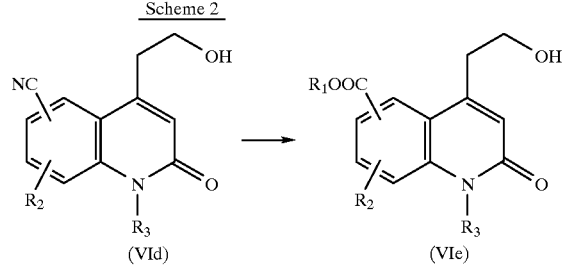

(VId)　　　　　　(VIe)

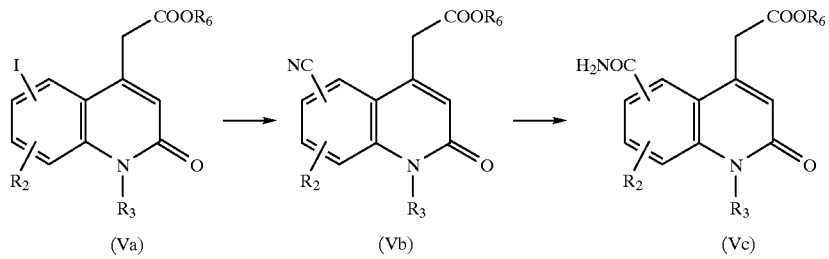

According to Scheme 3, a compound of formula (VIa), corresponding to a compound of formula (VI) (in which $R_1$ represents an iodine atom, $R_2$ is as defined above, $R_3$ is a hydrogen atom or a ($C_1$–$C_4$)alkyl group and m is equal to 2), is reacted with a thiolate such as sodium thiomethoxide, in the presence of tetrakis(triphenylphosphine)palladium[0] in an alcohol such as ethanol, propanol or n-butanol, to prepare a compound of formula (VIb) (in which $R_4$ is a ($C_1$–$C_4$)alkyl group), which may be converted by oxidation to a compound of formula (VIc).

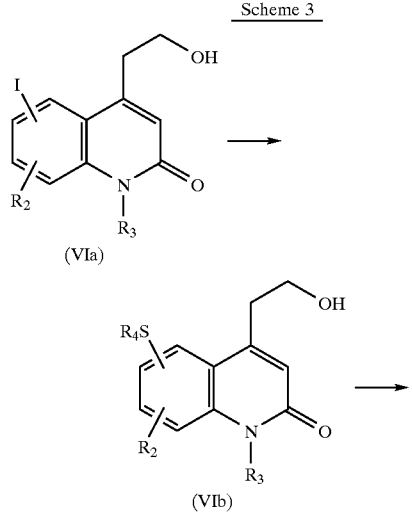

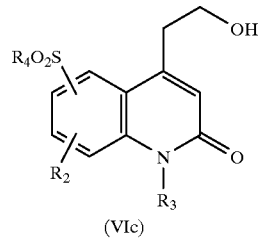

To obtain the compounds of formula (I) in which $R_1$ and/or $R_2$ represent (s) a nitro or amino group or a group —$NHCOR_4$, —$NHSO_2R_4$ or —$N(R_4)_2$, $R_4$ being a ($C_1$–$C_4$) alkyl group, the synthesis of the corresponding compounds of formula (VII) is conducted according to Scheme 4.

The nitration is carried out of a compound of formula (VIIa), corresponding to a compound of formula (VII) (in which $R_1$ is a hydrogen atom, X a halogen atom and $R_3$ a hydrogen atom or a ($C_1$–$C_4$)alkyl group), to obtain a compound of formula (VIIb), which is converted to a compound of formula (VIIc) by reduction with hydrogen, which compound is converted either to a compound of formula (VIId) by reaction with a carboxylic acid chloride of formula $R_4COCl$, or to a compound of formula (VIIe) by reaction with a sulphonic acid chloride of formula $R_4SO_2Cl$, or to a compound of formula (VIIf) by an N-dialkylation reaction. These compounds are then reacted with 4-(1-piperazinyl) thieno[3,2-c]pyridine or with 4-(4-fluorobenzoyl)piperidine according to Scheme 1.

Scheme 4

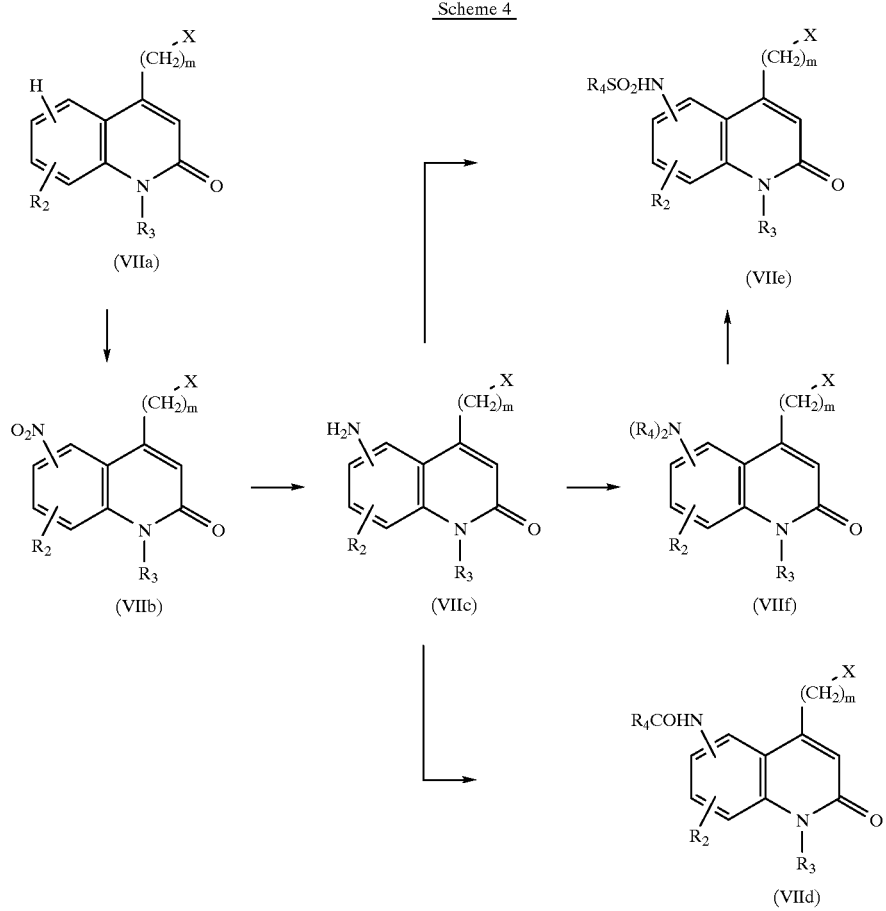

To prepare the compounds of formula (I) in which $R_1$ and/or $R_2$ represent(s) a hydroxyl group, a de-alkylation of the corresponding alkoxylated compound of formula (I) (in which $R_1$ and/or $R_2$ represent(s) an alkoxy group) may be carried out under standard conditions known to a person skilled in the art, such as, for example, a treatment with 48% hydrobromic acid.

The starting compounds are commercially available or described in the literature, or may be prepared according to methods which are described therein or which are known to a person skilled in the art.

Thus, 4-(acetyloxy)-2H,3H-pyran-2,6-dione is prepared from 3-oxoglutaric acid according to E. G. FRANDSEN and N. JACOBSEN, *J. Chem. Soc. Perkin I*, pp 933–6 (1978). The cyclization process is adapted from those described in European Patent Applications EP 0364327 and EP0577325. The introduction of a nitrile into the compounds of formula (V) is carried out according to the methodology described by N. CHANTANI and T. HANAFUSA, *J. Org. chem.* 51, pp 4714–4716 (1986).

The aromatic nucleophilic substitution of iodinated aryls with thiolates is based on the method of T. MIGITAL et al., *Bull. Chem. Soc. Japan*, 53, pp 1385 (1980).
4-(1-Piperazinyl)thieno[3,2-c]pyridine is synthesized according to J. S. NEW et al., *J. Med. Chem.* 32, No. 6, pp 1147–56 (1989).

The examples which follow illustrate the invention without limiting it. The microanalyses and the IR, NMR and mass spectra confirm the structure of the compounds obtained.

The numbers of the compounds exemplified refer to those in the table given later, which illustrates the chemical structures and the physical properties of a few compounds according to the invention.

The ratios (x:y) correspond to the (acid/base) ratio.

EXAMPLE 1 (COMPOUND NO. 27)

6-methoxy-4-[2-[4-(thieno[3,2-c]pyridin-4-yl)-1-piperazinyl]ethyl]-2(1H)-quinolone hydrochloride (2:1)

1.1. 3-(acetyloxy)-5-[(4-methoxyphenyl)methylamino]-5-oxo-2-pentenoic acid 27 g (158 mmol) of 4-(acetyloxy)-2H,3H-pyran-2,6-dione are added with vigorous stirring at room temperature to a solution of 20.0 g (146 mmol) of N-methyl-4-methoxyaniline in 100 ml of acetic acid. After 5 hours of stirring at room temperature, 700 ml of ice-cold water are added and the mixture is left stirring for 30 minutes. A beige solid is obtained, which is drained, washed with water, ground in diethyl ether and dried over phosphorus pentoxide at 40° C. for 24 hours.

28.1 g of product are obtained in the form of a solid.
Melting point=85–88° C.; Yield=76%

1.2. 6-methoxy-2-oxo-1,2-dihydro-4-quinolineacetic acid 41 g (133 mmol) of 3-(acetoxy)-5-[(4-methoxyphenyl)methylamino]-5-oxo-2-pentenoic acid are added in small portions to 70 ml of sulphuric acid (96–97%) at room temperature, and the mixture is then heated to 80° C. with stirring for 1 hour 30 minutes. After cooling, the reaction medium is poured into 100 g of ice and 100 ml of water, tle mixture is stirred for 15 minutes and the solid is drained and washed copiously with water before being dried for 48 hours at 50° C. 14.9 g of a mixture of 6-methoxy-1-methyl-2-oxo-1,2-dihydro-4-quinolineacetic acid and 6-methoxy-2-oxo-1,2-dihydro-4-quinolineacetic acid are collected.

Yield=45%

1.3. Methyl 6-methoxy-2-oxo-1,2-dihydro-4-quinolineacetate 16 ml (219 mmol) of thionyl chloride are added dropwise to a stirred suspension of 16.8 g (68 mmol) of a mixture of 6-methoxy-1-methyl-2-oxo-1,2-dihydro-4-quinolineacetic acid and 6-methoxy-2-oxo-1,2-dihydro-1-quinolineacetic acid in 250 ml of methanol at room temperature, and stirring is then maintained for 16 hours. The solvent is evaporated off under vacuum and the residue is taken up in 400 ml of dichloromethane. The mixture is washed with saturated sodium hydrogen carbonate solution and then with water and the organic phase is dried over sodium sulphate. After filtration and concentration, 12.6 g of a mixture of the two esters (71%) is obtained. The two esters are separated by flash chromatography on silica, eluting with a methanol/dichloromethane (3:97) mixture.

4.0 g of methyl 6-methoxy-1-methyl-2-oxo-1,2-dihydro-4-quinolineacetate, Melting point=129–130° C. and 7.8 g of methyl 6-methoxy-2-oxo-1,2-dihydro-4-quinolineacetate, Melting point=223–224° C. are obtained.

1.4. 4-(2-hydroxyethyl)-6-methoxy-2-(1H)-quinolone 1.4 g of sodium borohydride (37 mmol) are added to a suspension of 3.1 g (12.5 mmol) of methyl 6-methoxy-2-oxo-1,2-dihydroquinolineacetate in 100 ml of dry tetrahydrofuran and 1 ml of methanol at room temperature, and the reaction medium is heated to reflux for 16 hours. After cooling to 5° C., 1 ml of methanol is added dropwise, then, after 30 minutes, 0.5 g of sodium borohydride is added and the reaction medium is heated for a further 8 hours. After cooling and treatment with 5 ml of methanol, the solvents are evaporated off and the residue is taken up with 200 ml of dichloromethane and 100 ml of 1 N hydrochloric acid. The organic phase is separated, washed with water and dried over sodium sulphate. After filtration and concentration under vacuum, 1.95 g of the expected alcohol are obtained.

Yield=72%

1.5. 4-(2-chloroethyl)-6-methoxy-2(1H)-quinolone 3.4 ml (46.6 mmol) of thionyl chloride are added while stirring at room temperature to a suspension of 3.11 g (14.2 mmol) of 4-(2-hydroxyethyl)-6-methoxy-2(1H)-quinolone in 50 ml of chloroform and 3 drops of dimethylformamide. The suspension is heated to reflux for 14 hours (total solubilization). After cooling to room temperature, 50 ml of water are added dropwise to the reaction medium and the mixture is left stirring for 30 minutes. The organic phase is recovered, separated after settling has taken place, washed with water, dried over magnesium sulphate and filtered. The filtrate is concentrated under vacuum. 3.2 g of a pale yellow solid are obtained.

Melting point=231–232° C.; Yield=94%

1.6. 6-methoxy-4-[2-[4-(thieno[3,2-c]pyridin-4-yl)-1-piperazinyl]ethyl]-2(1H)-quinolone hydrochloride (2:1)

1.2 g (5 mmol) of 4-(2-chloroethyl)-6-methoxy-2(1H)-quinolone are added to a suspension of 1.2 g (5.5 mmol) of 4-(1-piperazinyl)thieno[3,2-c]pyridine and 0.44 g (5.25 mmol) of sodium hydrogen carbonate in 15 ml of acetonitrile, and the reaction mixture is then heated to reflux for 10 hours. After evaporation of the solvent under vacuum, the residue is taken up in 100 ml of dichloromethane and washed successively with saturated aqueous sodium bicarbonate solution and then with water. After drying over sodium sulphate, filtration and condensation of the filtrate, the crude product is purified by flash chromatography on silica, eluting with a methanol/dichloromethane (5:95) mixture containing traces of aqueous ammonia.

0.50 g of the product is obtained in base form.

Yield=24%

The dihydrochloride is prepared in a methanol/hydrochloric acid/ether mixture.

Melting point=254° C. (decomposition)

EXAMPLE 2 (COMPOUND NO. 28)

4-[2-[4-(4-fluorobenzoyl)-1-piperidyl]ethyl]-6-methoxy-2(1H)-quinolone hydrochloride (1:1)

A mixture of 1.1 g (4.6 mmol) of 4-(2-chloroethyl)-6-methoxy-2(1H)-quinolone, 1.0 g (5.5 mmol) of 4-(4-fluorobenzoyl)piperidine and 0.38 g (4.6 mmol) of sodium hydrogen carbonate in 20 ml of acetonitrile is heated to reflux for 8.5 hours. The reaction medium is then evaporated to dryness and the crude product is purified by flash chromatography on silica, eluting with a methanol/dichloromethane (5:95) mixture containing traces of aqueous ammonia.

0.53 g of the expected product is obtained in base form.

Yield=30%

The hydrochloride is prepared in a methanol/hydrochloric acid mixture.

Melting point=237° C. (decomposition)

EXAMPLE 3 (COMPOUND NO. 4)

6-chloro-4-[2-[4-(4-fluorobenzoyl)-1-piperidyl]ethyl]-1-methyl-2(1H)-quinolone hydrochloride (1:1)

3.1. 3-(acetyloxy)-5-[(4-chlorophenyl)methylamino]-5-oxo-2-pentenoic acid 19.8 g (116 mmol) of 4-(acetyloxy)-2H,3H-pyran-2,6-dione are added in small portions to a stirred solution of 15.0 g (106 mmol) of 4-chloro-N-methylbenzenamine in 40 ml of pure acetic acid. The reaction medium is stirred for 3 hours at 35° C. It is allowed to cool to room temperature and diluted in 10 ml of ice-cold water. The solid is drained, washed copiously with water and dried at 40° C. for 48 hours.

25.5 g of the expected compound are obtained in the form of an amorphous solid, which is used in the next step without further treatment.

Yield=77%

3.2. 6-chloro-1-methyl-2-oxo-1,2-dihydro-4-quinolineacetic acid 25.5 g (81.8 mmol) of 3-(acetyloxy)-5-[(4-chlorophenyl)methylamino]-5-oxo-2-pentenoic acid is introduced in small portions into 40 ml of concentrated sulphuric acid at room temperature with vigorous stirring, and the reaction medium is then heated to 85° C. for 60 minutes. After cooling, this solution is poured into a mixture of 500 g of ice and 500 ml of water. The grey solid thereby obtained is drained, washed with water, then ground in ether and dried for 24 hours at 40° C.

9.47 g of the expected product are obtained, which product is used in the next step without further treatment.

Yield=46%

3.3. Methyl 6-chloro-1-methyl-1,2-dihydro-4-quinolineacetate 11 ml (147 mmol) of thionyl chloride are added dropwise over approximately 30 minutes to a stirred suspension of 12.5 g (49 mmol) of 6-chloro-1-methyl-2-oxo-1,2-dihydro-4-quinolineacetic acid in 150 ml of methanol. The mixture is stirred for 17 hours at room temperature and the solvent is driven off under vacuum. The residue is dissolved in 400 ml of dichloromethane, and then washed with saturated aqueous sodium bicarbonate solution and then with water. After drying over sodium sulphate, the organic phase is filtered and the filtrate is condensed. 11.16 g of expected product are obtained.

Yield=85%; Melting point=99–101° C.

3.4. 6-chloro-4-(2-hydroxyethyl)-1-methyl-2(1H)-quinolone 3.0 g (79 mmol) of sodium borohydride are added to a suspension of 5.9 g (23.4 mmol) of methyl 6-chloro-1-methyl-1,2-dihydro-4-quinolineacetate in 10 ml of methanol and 100 ml of dry tetrahydrofuran, and the mixture is then heated to reflux for 9 hours. After cooling, the solvents are evaporated off under vacuum and the residue is taken up in 400 ml of dichloromethane and 100 ml of 3 N hydrochloric acid. The organic phase is washed with water, dried over sodium sulphate and filtered and the filtrate is condensed. The crude product is purified by flash chromatography on silica, eluting with a methanol/dichloromethane (5:95) mixture.

5.9 g of the expected alcohol are obtained.

Yield=92%; Melting point=169–170° C.

3.5. 6-chloro-4-(2-chloroethyl)-1-methyl-2(1H)-quinolone 5.5 ml (75 mmol) of thionyl chloride are added dropwise to a suspension of 5.9 g (24.8 mmol) of 6-chloro-4-(2-hydroxyethyl)-1-methyl-2(1H)-quinolone in 120 ml of chloroform, two drops of pyridine and two drops of dimethylformamide. The reaction medium is heated to a gentle reflux for 2.5 hours and then treated as described in Example 1.5.

5.4 g of the expected product are obtained.

Yield=86%; Melting point=120–122° C.

3.6. 6-chloro-4-[2-[4-(4-fluorobenzoyl)-1-piperidyl]ethyl]-1-methyl-2(1H)-quinolone hydrochloride (1:1)

A mixture of 0.90 g (3.5 mmol) of 6-chloro-4-(2-chloroethyl)-1-methyl-2(1H)-quinolone, 0.71 g (4.0 mmol) of 4-(4-fluorobenzoyl)piperidine and 0.60 g (7.0 mmol) of sodium bicarbonate in 15 ml of acetonitrile is heated to reflux for 11 hours. The reaction medium is then evaporated to dryness and the crude product is purified by flash chromatography on silica, eluting with a methanol/dichloromethane (4:96) mixture containing traces of aqueous ammonia.

0.86 g of the expected product are obtained in base form.

Yield=62%

The hydrochloride is prepared in a methanol/hydrochloric acid/ether mixture.

Melting point=244° C. (decomposition)

EXAMPLE 4 (COMPOUND NO. 5)

6-fluoro-1-methyl-4-[2-[4-(thieno[3,2-c]pyridin-4-yl)-1-piperazinyl]ethyl]-2(1H)-quinolone hydrochloride (2:1)

4.1. 3-(acetoxy)-5-[(4-fluorophenyl)methylamino]-5-oxo-2-pentenoic acid 9.93 g (58.4 mmol) of 4-(acetyloxy)-2H,3H-pyran-2,6-dione are added in small portions to a stirred solution of 6.64 g (53.1 mmol) of N-methyl-4-fluoroaniline in 25 ml of pure acetic acid. The reaction medium is stirred for 2 hours at 35° C., allowed to cool to room temperature and diluted in 500 ml of ice-cold water. The solid obtained is recovered and drained, washed copiously with water and dried in an oven (40° C.) for 48 hours.

12.05 g of the expected compound are obtained in the form of an amorphous solid, which melts below 50° C.

Yield=76%

4.2. 6-fluoro-1-methyl-2-oxo-1,2-dihydro-4-quinolineacetic acid 31.8 g (107 mmol) of 3-(acetyloxy)-5-[(4-fluorophenyl)methylamino]-5-oxo-2-pentenoic acid are introduced in small portions into 130 ml of concentrated sulphuric acid at room temperature with vigorous stirring, and the reaction medium is then heated to 90° C. for 90 minutes. After cooling, this solution is poured into a mixture of 500 g of ice and 500 ml of water. The grey solid thereby obtained is drained. It is washed with water, then ground in ether and dried for 24 hours at 40° C.

11.37 g of product are obtained.

Melting point=230° C.; Yield=45%

4.3. Methyl 6-fluoro-1-methyl-2-oxo-1,2-dihydro-4-quinolineacetate 16 ml (219 mmol) of thionyl chloride are added dropwise over approximately 30 minutes to a stirred suspension of 11.37 g (49.38 mmol) of a mixture of 6-fluoro-1-methyl-2-oxo-1,2-dihydro-4-quinolineacetic acid in 120 ml of methanol. The mixture is stirred overnight (13 hours) at room temperature and the solvent is driven off under vacuum. The residue is dissolved in 400 ml of dichloromethane, and then washed with saturated aqueous sodium bicarbonate solution and then with water. After drying over sodium sulphate, filtration and concentration of the filtrate, 9.6 g of the expected product are obtained.

Yield=78%; Melting point=134–135° C.

4.4. 6-fluoro-4-(2-hydroxyethyl)-1-methyl-2(1H)quinolone 3.78 g (100 mmol) of sodium borohydride are added to a suspension of 8.0 g (32 mmol) of methyl 6-fluoro-1-methyl-2-oxo-1,2-dihydro-4-quinolineacetate in 100 ml of dry tetrahydrofuran, and the mixture is heated to reflux for 20 hours. After cooling to 5° C., 2 ml of methanol are added dropwise, a further 3 g of sodium borohydride are added and the mixture is heated to reflux for 12 hours. The solvents are evaporated off under vacuum and the residue is taken up in 400 ml of dichloromethane and 150 ml of 2 N hydrochloric acid, the organic phase is washed with water, then dried over sodium sulphate and filtered and the filtrate is concentrated.

4.7 g of the expected alcohol are obtained.

Yield=66%; Melting point=153–154° C.

4.5 4-(2-chloroethyl)-6-fluoro-1-methyl-2(1H)-quinolone 3 ml (41 mmol) of thionyl chloride are added dropwise to a suspension of 2.2 g (9.95 mmol) of 6-fluoro-4-(2-hydroxyethyl)-1-methyl-2(1H)-quinolone in 100 ml of chloroform, two drops of pyridine and two drops of dimethylformamide. The reaction medium is heated to a gentle reflux for 4.5 hours. After cooling to room temperature, 50 ml of water are added dropwise to the reaction medium and the mixture is left stirring for 30 minutes. The organic phase is recovered, separated after settling has taken place, washed with water, dried over magnesium sulphate and filtered. The filtrate is concentrated under vacuum.

2.36 g of the expected chloride are obtained.

Yield=98%; Melting point=141–142° C.

4.6. 6-fluoro-1-methyl-4-[2-[4-(thieno[3,2-c]pyridine-4-yl)-1-piperazinyl]ethyl]-2(1H)-quinolone hydrochloride (2:1)

1.4 g (5.8 mmol) of 4-(2-chloroethyl)-6-fluoro-1-methyl-2(1H)-quinolone are added to a mixture of 1.3 g (5.9 mmol) of 4-(1-piperazinyl)thieno[3,2-c]pyridine and 0.50 g (5.95 mmol) of sodium hydrogen carbonate in 20 ml of acetonitrile, and the reaction medium is heated to 55–60° C. for 18 hours. The solvent is evaporated off and the residue is taken up in 100 ml of dichloromethane. It is washed with saturated aqueous sodium bicarbonate solution and then with water. The organic phase is dried over sodium sulphate and filtered and the filtrate is condensed. The crude product is purified by flash chromatography on silica, eluting with a methanol/dichloromethane (5:95) mixture containing traces of aqueous ammonia. 0.70 g of the expected product is obtained in base form.

Yield=27%

The base is dissolved in 10 ml of methanol and salified with an excess of a 2 N solution of hydrochloric acid in ether. The precipitate obtained is drained, recrystallized in methanol and dried under vacuum.

0.38 g of the dihydrochloride is obtained.

Melting point=280° C. (decomposition)

EXAMPLE 5 (COMPOUND NO. 10)

7-fluoro-2-oxo-4-[2-[4-(thieno[3,2-c]pyridin-4-yl)-1-piperazinyl]ethyl]-1,2-dihydro-1-quinolineacetic acid hydrochloride (2:1)

2.9 ml of a 0.5 M solution of tert-butyl bromoacetate in tetrahydrofuran are added dropwise to a mixture of 0.50 g (1.23 mmol) of 7-fluoro-4-[2-[4-(thieno[3,2-c]pyridin-4-yl)-1-piperazinyl]ethyl]-2(1H)quinolone (prepared from 3-fluoroaniline according to the method described in Example 4), 0.10 g (1.79 mmol) of freshly ground potassium hydroxide and 0.12 g (0.37 mmol) of tetrabutylammonium bromide in 20 ml of tetrahydrofuran at 0–5° C. After 30 minutes at 0–5° C., the temperature is allowed to rise to room temperature and stirring is continued for 6 hours. The solvent is evaporated off under vacuum and the residue is taken up in 100 ml of dichloromethane, and the organic phase is washed with water, dried over sodium sulphate and condensed. The crude product is purified by flash chromatography on silica, eluting with a methanol/dichloromethane (5:95) mixture containing traces of aqueous ammonia, and 0.48 g of tert-butyl N-acetate is obtained in the form of a thick, colorless oil.

Yield=75%

50 ml of a 3 N solution of hydrochloric acid in ethyl acetate are added to this oil, and the mixture is stirred at room temperature for 4 hours. It is evaporated to dryness, and the white solid obtained is ground with ether and dried under vacuum.

0.47 g of the expected acid are obtained in the form of the dihydrochloride.

Yield=87%; Melting point=218–220° C. (decomposition)

EXAMPLE 6 (COMPOUND NO. 12)

7-fluoro-2-oxo-4-[2-[4-(thieno[3,2-c]pyridin-4-yl)-1-piperazinyl]ethyl]-1,2-dihydro-1-quinolineacetamide hydrochloride (2:1)

3.9 ml of a 0.5 M solution of bromoacetamide in tetrahydrofuran are added dropwise to a stirred mixture of 0.53 g (1.3 mmol) of 7-fluoro-4-[2-[4-(thieno[3,2-c]pyridin-4-yl) ethyl]-2(1H)-quinolone, 0.1 g (1.79 mmol) of ground potassium hydroxide and 0.13 g (0.4 mmol) of tetrabutylammonium bromide in 25 ml of tetrahydrofuran at 0–5° C. After 30 minutes, the temperature is allowed to rise to room temperature and the mixture is stirred at this temperature for 20 hours. The reaction medium is evaporated to dryness under vacuum and the residue is taken up in 100 ml of dichloromethane. This solution is washed with water. The organic phase is dried over magnesium sulphate and concentrated. The crude product is ground in an ether/dichloromethane (1:3) mixture, and the solid is then drained and purified by chromatography on silica, eluting with a methanol/ethyl acetate (10:90) mixture and then with a methanol/dichloromethane (10:90) mixture containing traces of aqueous ammonia.

0.303 g of a white solid is obtained, which solid is converted to a dihydrochloride in a 2 M hydrochloric acid/ether/methanol mixture.

0.32 g of dichlorohydride is obtained.

Melting point=280° C. (decomposition)

Example 7 (COMPOUND NO. 20)

1-methyl-2-oxo-4-[2-[4-(thieno[3,2-c]pyridin-4-yl)-1-piperazinyl]ethyl]-1,2-dihydro-6-quinolinecarbonitrile hydrochloride (2:1)

7.1. Methyl 6-cyano-1-methyl-2-oxo-1,2-dihydro-4-quinolineacetate 1.1 ml of trimethylsilyl cyanide (8.4 mmol) followed by 0.15 g (0.13 mmol) of tetrakistriphenylphosphinepalladium are added to a solution of 0.50 g (1.4 mmol) of methyl 6-iodo-1-methyl-2-oxo-1,2-dihydro-4-quinolineacetate (prepared from N-methyl-4-iodoaniline according to the method described in Example 1) in 6 ml of anhydrous triethylamine. The reaction medium is then heated to reflux for 4 hours under a nitrogen atmosphere. After cooling to room temperature, the medium is poured into 60 ml of toluene and 60 ml of water. The organic phase is washed with water and the initial aqueous phase is re-extracted with dichloromethane. The organic phases are combined, dried over sodium sulphate and concentrated under vacuum. The residue is purified by flash chromatography on silica, eluting with a methanol/dichloromethane (5:95) mixture.

0.313 g of the expected nitrile is obtained.

Yield=87%; Melting point=202–203° C.

7.2 6-cyano-4-(2-hydroxyethyl)-1-methyl-2(1H)-quinolone 7.2.1. 6-cyano-1-methyl-2-oxo-1,2-dihydro-4-quinolineacetic acid 10.4 ml of a 0.5 N solution of lithium hydroxide (5.2 mmol) are added dropwise to 1.21 g (4.7 mmol) of methyl 6-cyano-1-methyl-2-oxo-1,2-dihydro-4-quinolineacetate in 10 ml of methanol at 0–5° C. The temperature is allowed to rise to room temperature and the reaction medium is stirred for 2 hours. It is poured into 250 ml of ice-cold water and acidified to pH 2–3 with 4 N hydrochloric acid. The white precipitate formed is drained, washed with water and then dried under vacuum at 40° C.

0.85 g of the expected product is obtained.

Yield=75%; Melting point=238° C.

7.2.2. 6-cyano-4-(2-hydroxyethyl)-1-methyl-2(1H)-quinolone 0.22 ml (1.58 mmol) of triethylamine is added to a suspension of 0.365 g (1.51 mmol) of 6-cyano-1-methyl-2-oxo-1,2-dihydro-4-quinolineacetic acid in 10 ce of tetrahydrofuran at −10° C., and 0.16 ml (1.6 mmol) of ethyl choroformate is then added dropwise. After stirring at −10° C. for 45 minutes, the reaction medium is filtered and the solids are rinsed with 3×8 ml of tetrahydrofuran. 0.25 g (6.61 mmol) of sodium borohydride and then 0.94 ml of methanol are added to the filtrate at 5–10° C. After stirring at 5–10° C. for 2 hours, 13 ml of 1 N aqueous hydrochloric acid solution are added. The mixture is extracted with is dichloromethane and then with ethyl acetate. The organic phases are dried over sodium sulphate and then concentrated under vacuum.

0.315 g of product is obtained.

Yield=92%;

Melting point=231–233° C.

7.3. 4-(2-bromoethyl) -6-cyano-1-methyl-2(1H)-quinolone 0.24 g (1.05 mmol) of 6- cyano-4-(2-hydroxyethyl)-1-methyl-2(1H)-quinolone is added in small amounts to 0.48 g (1.14 mmol) of dibromotriphenylphosphorane in 14 ml of dichdoromethane at room temperature. After 75 minutes of stirring at room temperature, the reaction medium is poured into 200 ml of dichloromethane and the mixture is washed with water. The organic phase is dried over sodium sulphate, filtered and condensed under vacuum. The white residue is ground in diethylether. The solid obtained is taken up in a minimum of dichloromethane, the mixture is filtered rapidly through a layer of silica, eluting with ether, and the filtrate is evaporated.

0.20 g of product is obtained, which product is used without further treatment.

Yield=65%

7.4. 1-methyl-2-oxo-4-[2-[4-(thieno[3,2-c]pyridin-4-yl)-1-piperazinyl]ethyl]-2(1H)-quinolone hydrochloride (2:1)

A mixture of 0.19 g (0.65 mmol) of 4-(2-bromoethyl)-6-cyano-1-methyl-2-(1H)-quinolone, 0.15 g (0.65 mmol) of 4-(1-piperazinyl)thieno[3,2-c]pyridine and 0.09 g (0.11 mmol) of sodium bicarbonate in 10 ml of acetonitrile is heated to 55° C. for 36 hours. The reaction medium is evaporated to dryness, the residue is taken up in 100 ml of chloroform and the organic phase is washed with water. It is dried over sodium sulphate and concentrated and the crude product is purified by flash chromatography on silica, eluting with a methanol/dichloromethane (1:9) mixture containing traces of aqueous ammonia.

0.211 g of base is obtained in the form of a colorless oil.

Yield=48%

The dihydrochloride is prepared in a methanol/ether/2 N hydrochloric acid mixture.

0.182 g of product is obtained in the form of the dihydrochloride.

Melting point=200° C. (decomposition)

EXAMPLE 8 (COMPOUND NO. 17)

6-hydroxy-1-methyl-4-[2-[4-(thieno[3,2-c]pyridin-4-yl)-1-piperazinyl]ethyl]-2(1H)-quinolone hydrochloride (2:1)

0.47 g (1.08 mmol) of 6-methoxy-1-methyl-4-[2-[4-(thieno[3,2-c]pyridin-4-yl)-1-piperazinyl]ethyl]-2(1H)-quinolone (obtained from methyl 6-methoxy-1-methyl-2-oxo-1,2-dihydro-4-quinolineacetate according to Example 1) is added to 25 ml of 48% hydrobromic acid, and the mixture is brought to reflux for 3 hours. After cooling, the grey precipitate is filtered off, washed with cold water and dried under vacuum at 40° C. 0.444 g of the product is obtained in the form of the dihydrobromide.

Yield=71%

0.14 g (0.24 mmol) of this product is taken up in 20 ml of 3.7 N hydrochloric acid in anhydrous methanol, and the mixture is stirred at room temperature for 3 hours. The precipitate is drained, rinsed with diethylether and dried in an oven.

0.112 g of the expected product is obtained.

Yield=95%; Melting point=227° C. (decomposition)

EXAMPLE 9 (COMPOUND NO. 18)

6-nitro-4-[2-[4-(thieno[3,2-c]pyridin-4-yl)-1-piperazinyl]ethyl]-2(1H)-quinolone hydrochloride (2:1)

9.1. 4-(2-chloroethyl)-6-nitro-2(1H)-quinolone 20.0 g (96.4 mmol) of 4-(2-chloroethyl)-2(1H)-quinolone is added in small amounts to a mixture of 120 ml of 65% nitric acid and 80 ml of concentrated sulphuric acid cooled to 5° C., and the mixture is heated to 45° C. for 2 hours. The reaction medium is poured into 600 ml of ice-cold water, and the pale yellow precipitate is drained, rinsed with water and dried under vacuum.

22.5 g of expected product are obtained.

Yield=92%; Melting point=239–237° C.

9.2 6-nitro-4-[2-[4-(thieno[3,2-c]pyridin-4-yl)-1-piperazinyl]ethyl]-2(1H)-quinolone hydrochloride (2:1)

A mixture of 1 g (3.96 mmol) of 4-(2-chloroethyl)-6-nitro-2(1H)-quinolone, 0.87 g (4 mmol) of 4-(1-piperazinyl) thieno[3,2-c]pyridine and 0.5 g (5.95 mmol) of sodium bicarbonate in 10 ml of dimethylformamide is heated to 50° C. for 20 hours. The residue is then filtered off and washed with water, 200 ml of water are added to the filtrate and the precipitate formed is drained and dried under vacuum.

1.28 g of the expected product are obtained in base form.

Yield=74%

The hydrochloride is prepared in a methanol/etherohydrochloric acid mixture.

Melting point=242° C. (decomposition)

EXAMPLE 10 (COMPOUND NO. 16)

6-amino-4-[2-[4-(thieno[3,2-c]pyridin-4-yl)-1-piperazinyl]ethyl]-2(1H)-quinolone hydrochloride (3:1)

10.1. 6-amino-4-(2-chloroethyl)-2(1H)-quinolone hydrochloride (1:1)

0.70 g of palladium on charcoal (5% Pd) is added to a suspension of 3.5 g (13.8 mmol) of 4-(2-chloroethyl)-6-nitro-2(1H)-quinolone in 300 ml of methanol at room temperature, and the mixture is stirred under a hydrogen pressure of 8 psi (0.06 MPa) for 3 hours. The catalyst is filtered off and the filtrate is condensed.

2.97 g of the product are obtained in base form.

The hydrochloride is prepared in a methanol/ether/hydrochloric acid mixture.

Melting point>290° C.

10.2. 6-amino-4-[2-[4-(thieno[3,2-c]pyridin-4-yl)-1-piperazinyl]ethyl]-2(1H)-quinolone hydrochloride (3:1)

A mixture of 0.35 g (1.35 mmol) of 6-amino-4-(2-chloroethyl)-2(1H)-quinolone hydrochloride, 0.33 g (1.5 mmol) of 4-(1-piperazinyl)thieno[3,2-c]pyridine and 0.17 g (2 mmol) of sodium bicarbonate in 10 ml of dimethylformamide is heated to 60° C. for 24 hours. After cooling to room temperature, the reaction medium is diluted in 50 ml of water and the crude product is extracted with chloroform. The organic phase is dried over sodium sulpbate and concentrated. The crude product is purified by flash chromatography on silica, eluting first with a methanol/ethyl acetate (6.5:93.5) mixture containing traces of triethylamine and then with a methanol/dichloromethane (6.5:93.5) mixture comprising traces of aqueous ammonia.

0.14 g of product is obtained in base form.

Yield=26%

The trihydrochloride is then prepared under standard conditions.

Melting point=233° C. (decomposition)

EXAMPLE 11 (COMPOUND NO. 33)

6-acetylamino-4-[2-[4-(thieno[3,2-c]pyridin-4-yl)-1-piperazinyl]ethyl]-2(1H)-quinolone hydrochloride (2:1)

11.1. 6-acetylamino-4-(2-chloroethyl)-2(1H)-quinolone hydrochloride (1:1)

0.75 ml (5.39 mmol) of triethylamine and then 0.35 ml (4.9 mmol) of acetyl chloride are added to a suspension of 1.0 g (4.49 mmol) of 6-amino-4-(2-chloroethyl)-2(1H)-quinolone in 50 ml of chloroform at room temperature. The mixture is stirred for 16 hours and then diluted in 200 ml of chloroform. The suspension is washed with 1 N aqueous hydrochloric acid solution and the precipitate is drained.

0.72 g of the expected product is obtained.
Yield=60%

11.2. 6-acetylamino-4-[2-[4-(thieno[3,2-c]pyridin-4-yl)-1-piperazinyl]ethyl]-2(1H)-quinolone hydrochloride (2:1)

A mixture of 0.35 g (1.32 mmol) of 6-acetylamino-4-(2-chloroethyl)-2(1H)-quinolone hydrochloride, 0.38 g (1.75 mmol) of 4-(1-piperazinyl)thieno[3,2-c]pyridine and 0.17 g (2 mmol) of sodium bicarbonate in 10 ml of dimethylformamide is heated to 60° C. for 24 hours. After cooling to room temperature, the reaction medium is diluted in 100 ml of water and left standing overnight at 5° C. The solid formed is drained and dried under vacuum. The crude product is purified by flash chromatography on silica, eluting first with a methanol/ethyl acetate (5:95) mixture and then with a methanol/dichloromethane (10:90) mixture comprising traces of aqueous ammonia.

0.20 g of product is obtained in base form.
Yield=34%

The dihydrochloride is then prepared under standard conditions.

Melting point=225° C. (decomposition)

Legend to the table:
in the "Salt" column:
HCl represents a hydrochloride,
the ratios (x:y) correspond to the (acid/base) ratio,
where no entry is present, this means that the compound is in base form.
in the "Melting point" column:
"(d)" corresponds to melting with decomposition.

TABLE (I)

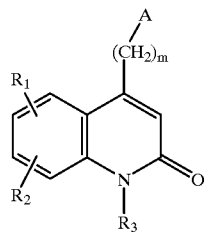

| No. | $R_1$ | $R_2$ | $R_3$ | m | A | Salt | Melting point (° C.) |
|---|---|---|---|---|---|---|---|
| 1 | —H | —H | —H | 2 | (piperazinyl-thieno[3,2-c]pyridine) | HCl (2:1) | 251 (d) |
| 2 | —H | —H | —CH$_2$CONH$_2$ | 2 | (piperazinyl-thieno[3,2-c]pyridine) | HCl (2:1) | 274 (d) |
| 3 | 6-Cl | —H | —CH$_3$ | 2 | (piperazinyl-thieno[3,2-c]pyridine) | HCl (2:1) | 277 (d) |

TABLE-continued
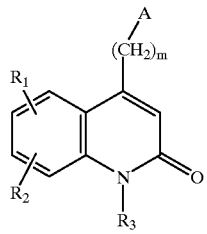
(I)
| No. | R₁ | R₂ | R₃ | m | A | Salt | Melting point (° C.) |
|---|---|---|---|---|---|---|---|
| 4 | 6-Cl | —H | —CH₃ | 2 | 4-(4-fluorobenzoyl)-1-methylpiperidine | HCl (1:1) | 244 (d) |
| 5 | 6-F | —H | —CH₃ | 2 | 4-(4-methylpiperazin-1-yl)thieno[3,2-c]pyridine | HCl (2:1) | 280 (d) |
| 6 | 7-Cl | —H | —H | 2 | 4-(4-methylpiperazin-1-yl)thieno[3,2-c]pyridine | HCl (2:1) | 240 (d) |
| 7 | 7-Cl | —H | —H | 2 | 4-(4-fluorobenzoyl)-1-methylpiperidine | HCl (1:1) | 263 (d) |
| 8 | 7-F | —H | —H | 2 | 4-(4-methylpiperazin-1-yl)thieno[3,2-c]pyridine | HCl (2:1) | 252 (d) |
| 9 | 7-F | —H | —CH₂CH₂OH | 2 | 4-(4-methylpiperazin-1-yl)thieno[3,2-c]pyridine | HCl (2:1) | 196 (d) |

TABLE-continued (I)

| No. | R₁ | R₂ | R₃ | m | A | Salt | Melting point (° C.) |
|-----|-----|-----|-----|---|---|------|----------------------|
| 10 | 7-F | —H | —CH₂COOH | 2 | 4-(4-methylpiperazin-1-yl)thieno[3,2-c]pyridine | HCl (2:1) | 218 (d) |
| 11 | 7-F | —H | —CH₂COOC(CH₃)₃ | 2 | 4-(4-methylpiperazin-1-yl)thieno[3,2-c]pyridine | — | oil |
| 12 | 7-F | —H | —CH₂CONH₂ | 2 | 4-(4-methylpiperazin-1-yl)thieno[3,2-c]pyridine | HCl (2:1) | 280 (d) |
| 13 | 7-F | —H | —CH₂CONH₂ | 2 | (1-methylpiperidin-4-yl)(4-fluorophenyl)methanone | HCl (1:1) | 245 (d) |
| 14 | 7-F | —H | —CH₂CONHCH₃ | 2 | 4-(4-methylpiperazin-1-yl)thieno[3,2-c]pyridine | HCl (2:1) | 260 (d) |
| 15 | 7-F | —H | —CH₂CH₂OCOCH₃ | 2 | 4-(4-methylpiperazin-1-yl)thieno[3,2-c]pyridine | HCl (2:1) | 225 (d) |

TABLE-continued (I)

| No. | R₁ | R₂ | R₃ | m | A | Salt | Melting point (°C.) |
|---|---|---|---|---|---|---|---|
| 16 | 6-NH₂ | —H | —H | 2 | (4-methylpiperazinyl)-thieno[3,2-c]pyridine | HCl (3:1) | 233 (d) |
| 17 | 6-OH | —H | —CH₃ | 2 | (4-methylpiperazinyl)-thieno[3,2-c]pyridine | HCl (2:1) | 227 (d) |
| 18 | 6-NO₂ | —H | —H | 2 | (4-methylpiperazinyl)-thieno[3,2-c]pyridine | HCl (2:1) | 242 (d) |
| 19 | 6-NO₂ | —H | —H | 2 | (1-methylpiperidin-4-yl)(4-fluorophenyl)methanone | HCl (1:1) | 250 (d) |
| 20 | 6-CN | —H | —CH₃ | 2 | (4-methylpiperazinyl)-thieno[3,2-c]pyridine | HCl (2:1) | 200 (d) |
| 21 | 6-CH₃ | —H | —H | 2 | (4-methylpiperazinyl)-thieno[3,2-c]pyridine | HCl (2:1) | 235 (d) |

TABLE-continued

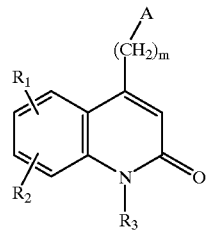

(I)

| No. | R₁ | R₂ | R₃ | m | A | Salt | Melting point (° C.) |
|---|---|---|---|---|---|---|---|
| 22 | 6-CH₃ | —H | —H | 2 | 1-methylpiperidin-4-yl (4-fluorophenyl) ketone | HCl (1:1) | 275 (d) |
| 23 | 6-CH₃ | —H | —CH₃ | 2 | 4-(4-methylpiperazin-1-yl)thieno[3,2-c]pyridine | HCl (2:1) | 243 (d) |
| 24 | 6-CH(CH₃)₂ | —H | —H | 2 | 4-(4-methylpiperazin-1-yl)thieno[3,2-c]pyridine | HCl (2:1) | 192 (d) |
| 25 | 6-CH(CH₃)₂ | —H | —H | 2 | 1-methylpiperidin-4-yl (4-fluorophenyl) ketone | HCl (1:1) | 169 (d) |
| 26 | 6-CH₃ | —H | —CH₂COOH | 2 | 4-(4-methylpiperazin-1-yl)thieno[3,2-c]pyridine | HCl (2:1) | 204 (d) |
| 27 | 6-OCH₃ | —H | —H | 2 | 4-(4-methylpiperazin-1-yl)thieno[3,2-c]pyridine | HCl (2:1) | 254 (d) |

TABLE-continued (I)

| No. | R₁ | R₂ | R₃ | m | A | Salt | Melting point (°C.) |
|---|---|---|---|---|---|---|---|
| 28 | 6-OCH₃ | —H | —H | 2 | (1-methylpiperidin-4-yl)(4-fluorophenyl)methanone | HCl (1:1) | 237 (d) |
| 29 | 6-OCH₃ | —H | —CH₃ | 2 | 4-(4-methylpiperazin-1-yl)thieno[3,2-c]pyridine | HCl (2:1) | 240 (d) |
| 30 | 7-OCH₃ | —H | —H | 2 | 4-(4-methylpiperazin-1-yl)thieno[3,2-c]pyridine | — | 204 (d) |
| 31 | 7-OCH₃ | —H | —CH₂CONH₂ | 2 | 4-(4-methylpiperazin-1-yl)thieno[3,2-c]pyridine | — | 228 (d) |
| 32 | 6-OCF₃ | —H | —CH₃ | 2 | 4-(4-methylpiperazin-1-yl)thieno[3,2-c]pyridine | HCl (2:1) | 156 (d) |
| 33 | 6-NHCOCH₃ | —H | —H | 2 | 4-(4-methylpiperazin-1-yl)thieno[3,2-c]pyridine | HCl (2:1) | 225 (d) |

TABLE-continued (I)

| No. | R₁ | R₂ | R₃ | m | A | Salt | Melting point (° C.) |
|---|---|---|---|---|---|---|---|
| 34 | 6-NHSO$_2$CH$_3$ | —H | —H | 2 | piperazinyl-thieno[3,2-b]pyridine | HCl (2:1) | >250 |
| 35 | 6-N(CH$_3$)$_2$ | —H | —H | 2 | piperazinyl-thieno[3,2-b]pyridine | HCl (3:1) | 210 (d) |

The compounds of the invention were subjected to pharmacological studies which demonstrated their serotonin-antagonist properties and their value as substances having therapeutic activity.

Thus, the compounds of the invention were subjected to a test of inhibition of the vasopressor effect of serotonin. Male rats (Sprague-Dawley, Charles River France) weighing 250 to 300 g are used, which are anaesthetized with pentobarbitone sodium (60 mg/kg/i.p.) and maintained under artificial respiration (Harvard™ respirator—respiratory rate 70 ml per minute, air volume 1 ml per 100 g body weight). The animals are pithed using a metal rod, introduced via the orbit of the right eye, inserted along the vertebral column. The right and left vagus nerves are sectioned (bivagotomy) and the right carotid artery is ligated, the left carotid artery being catheterized in order to measure the arterial blood pressure using a pressure cell (Statham™ type P23Db). A femoral vein is catheterized for the purpose of administration of various compounds. The increases in mean arterial blood pressure induced by serotonin, administered intravenously at a dose of 30 μg/kg, are measured. The compounds of the invention or the vehicle are administered 5 minutes (for the studies via the i.v. route) or 75 minutes (for the studies via the oral route) before the administration of serotonin. The compounds of the invention are administered at doses ranging from 0.001 to 10 mg/kg. The percentage inhibition of the control response to serotonin is used in order to assess the serotonin-antagonist potential of the compounds of the invention.

The compounds of the invention were also tested in a model of sumatriptan vasoconstriction of isolated dog saphenous vein (antagonist activity at the 5-HT$_1$-like receptor, according to HUMPHREY et al. in Br. J. Pharmacol. 1988, 94, 1123).

Saphenous veins of beagle or Anglo-Poitevin dogs are removed under pentobarbitone anaesthesia administered by intravenous injection. The vessel is cut into spirals 0.4 cm in width and then divided into segments 0.5 cm in length. Each fragment, mounted between two cable clamps, is placed in an isolated-organ cell containing 20 ml of a Krebs physiological solution of the following composition (mM): NaCl 118; KCl 4.7; MgCl$_2$ 1.2; CaCl$_2$ 2.6; NaHCO$_3$ 25; glucose 11.1; ascorbic acid 0.11. The organ, maintained at 37° C. under a stream of carbogen (95% O$_2$/5% CO$_2$) at pH 7.4, is linked to a Hugo Sachs type 351 isometric gauge under a baseline tension of 2 g, and connected to a Gould 2400S polygraph enabling the tension changes to be recorded. Data acquisition is automated via a microcomputer system. After a period of 90 minutes at rest interspersed with frequent rinses, during which the baseline tension is readjusted, the organ is stimulated with 3 μM noradrenaline in order to check its viability. A curve is then constructed of concentration versus contractile response to sumatriptan in cumulative fashion between 10 nM and 10 μM. When the maximal contraction is obtained (plateau of the effect at two consecutive concentrations of sumatriptan), the preparation is rinsed copiously, interspersing periods of rest to enable the organ to return to the initial tension. The compound under study is then added to the organ bath 15 minutes before a second concentration-response to sumatriptan curve is constructed. The contractile responses obtained in the presence of the compound are expressed as a percentage of the maximal contraction observed in the first sumatriptan curve. The curves are analysed by non-linear regression so as is to determine the $E_{max}$ (maximal response) and the $EC_{50}$ (concentration producing 50% of the maximal response). The antagonist potential of the compounds is estimated by calculating the dissociation constant $K_B$ according to the equation $K_B$=[concentration of the compound in M]/(CR−1) where CR represents the ratio of the sumatriptan $EC_{50}$ values in the presence and absence of the compound. The result is expressed as $pA_2$=−log KB. The $pA_2$ values of the compounds of the invention are greater than 6.

The compounds of the invention were also subjected to a test of inhibition of the binding of [$^3$H]spiroperidol to the 5-HT$_2$ serotoninergic receptors of rat cerebral cortex. For this test, rat brains are removed and the cortex is dissected out and homogenized at 0° C. in 20 volumes of a mixture containing, per liter, 50 mmol of Tris-HCl buffer at pH 7.4, 120 mmol of NaCl and 5 mmol of KCl. The homogeneous mixture is centrifuged at 40000×g for 10 minutes and then, twice, the pellet is recovered, washed by suspending it in the same buffer mixture, homogenized again and centrifuged. Lastly, the final pellet is diluted in the same buffer mixture in the proportion of 500 mg of wet tissue for 10 ml of buffer. The tissue is then subjected to a prior incubation for 10 minutes at 37° C. in the presence of 10 μmol/l of pargyline, and thereafter to an incubation for 20 minutes at 37° C. in the presence of [$^3$H]spiroperidol (specific activity: 19 Ci per mmol) at a concentration of 0.3 nM and of compound under study at concentrations ranging from 0.0001 to 100 μM.

1-ml aliquots are sampled and filtered under vacuum, the filters are washed twice with 5 ml of cold buffer and dried and the radioactivity is measured.

To evaluate the activity of the compounds, the curve is plotted for the percentage inhibition of specific binding of [$^3$H]spiroperidol as a function of the concentration of displacing drug. The $IC_{50}$, the concentration which inhibits 50% of the specific binding, is determined graphically.

The specific binding is defined as the binding displaced by 100 μM 5-HT.

The $IC_{50}$ values of the compounds of the invention are less than 1 μM.

The results of these tests showed that the compounds of the invention display serotonin-antagonist properties.

On this basis, these may be used in the treatment and prevention of various forms of pathologies involving serotonin, such as arterial, venous, pulmonary, portal, renal or ocular hypertension, cardiac, renal, ocular or cerebral ischaemia or ischaemia of the lower limbs, cardiac insufficiency, myocardial infarction, angina, coronary or peripheral vasospasm, thrombosis (the compounds on their own or as adjuvants in thrombolysis), arteritis, intermittent claudication, restenosis after angioplasty and various pathological states associated with atherosclerosis, with disorders of the microcirculation or with pulmonary dysfunction. They may also be used, alone or in combination with other substances, in vascular grafting operations.

The compounds of the invention may be used in combination with other substances having cardiovascular or cardiopulmonary activity, such as antithrombotics, thrombolytics, β-blockers, calcium antagonists, thromboxane antagonists and thromboxane synthetase inhibitors.

For this purpose, these compounds may be presented in all forms suitable for oral or parenteral administration, such as tablets, dragees, capsules including hard gelatin capsules and topical ocular formulations, in combination with suitable excipients. The doses present in these forms are such as to permit an administration of 0.1 mg to 1 g, one to several times daily.

They may also be presented in all forms suitable for transdermal administration.

We claim:
1. A compound of formula (I)

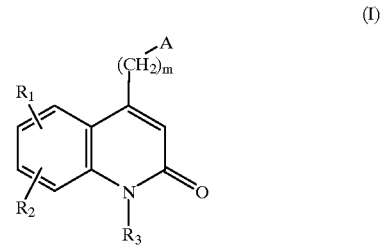

in which
A represents either a 4-(thieno[3,2-c]pyridin-4-yl)-1-piperazinyl group or a 4-(4-fluorobenzoyl)-1-piperidyl group,
$R_1$ and $R_2$ each represent, independently of one another, either a hydrogen atom, or a halogen atom, or an amino group, or a hydroxyl group, or a nitro group, or a cyano group, or a $(C_1-C_6)$alkyl group, or a $(C_1-C_6)$alkoxy group, or a trifluoromethyl group, or a trifluoromethoxy group, or a —COOH group, or a group —COOR$_4$, or a —CONH$_2$ group, or a group —CONHR$_4$, or a group —CONR$_4$R$_5$, or a group —SR$_4$, or a group —SO$_2$R$_4$, or a group —NHCOR$_4$, or a group —NHSO$_2$R$_4$, or a group —N(R$_4$)$_2$, where $R_4$ and $R_5$ are each a $(C_1-C_4)$alkyl group,
$R_3$ represents either a hydrogen atom, or a $(C_1-C_4)$alkyl group, or a group —(CH$_2$)$_p$OH, or a group —(CH$_2$)$_p$NH$_2$, or a group —(CH$_2$)$_n$COOH, or a group —(CH$_2$)$_n$COOR$_4$, or a group —(CH$_2$)$_n$CONH$_2$, or a group —(CH$_2$)$_n$CONHOH, or a group —(CH$_2$)$_p$SH, or a group —(CH$_2$)$_n$SO$_3$H, or a group —(CH$_2$)$_n$SO$_2$NH$_2$, or a group —(CH$_2$)$_n$SO$_2$NHR$_4$, or a group —(CH$_2$)$_n$SO$_2$NR$_4$R$_5$, or a group —(CH$_2$)$_n$CONHR$_4$, or a group —(CH$_2$)$_n$CONR$_4$R$_5$, or a group —(CH$_2$)$_p$NHSO$_2$R$_4$, or a group —(CH$_2$)$_p$NHCOR$_4$, or a group —(CH$_2$)$_p$OCOR$_4$, where $R_4$ and $R_5$ are each a $(C_1-C_4)$alkyl group, n is equal to 1, 2, 3 or 4, p is equal to 2, 3 or 4 and m is equal to 2, 3 or 4, as well as their addition salts with pharmaceutically acceptable acids or bases.
2. The compound according to claim 1, wherein is equal to 2.
3. The compound according to claim 1 wherein $R_1$, at position 6 or 7 on the quinolone represents either a hydrogen, fluorine or chlorine atom, or an amino, hydroxyl, nitro, cyano, $(C_1-C_6)$alkyl, methoxy, trifluoromethoxy, acetylamino, methylsulphonylamino or dimethylamino group, and $R_2$ represents a hydrogen atom.
4. The compound according to claim 1 wherein $R_3$ represents either a hydrogen atom, or a $(C_1-C_4)$alkyl group, or a group —(CH$_2$)$_p$OH, or a group —(CH$_2$)$_n$COOH, or a group —(CH$_2$)$_n$COOR$_4$, or a group —(CH$_2$)$_n$CONH$_2$, or a group —(CH$_2$)$_n$CONHR$_4$, or a group —(CH$_2$)$_n$CONR$_4$R$_5$, or a group —(CH$_2$)$_p$OCOR$_4$ where $R_4$ and $R_5$ are each a $(C_1-C_4)$alkyl group, n is equal to 1, 2, 3 or 4 and p is equal to 2, 3 or 4.
5. The compound according to claim 1 wherein n is equal to 1 and p is equal to 2.
6. The compound according to claim 1 selected from the group consisting of:
6-fluoro-1-methyl-4-[2-[4-(thieno[3,2-c]pyridin-4-yl)-1-piperazinyl]ethyl]-2(1H)-quinolone,
7-fluoro-2-oxo-4-[2-[4-(thieno[3,2-c]pyridin-4-yl)-1-piperazinyl]ethyl]-1,2-dihydro-1-quinolineacetamide, 7-fluoro-N-methyl-2-oxo-4-[2-[4-(thieno[3,2-c]pyridin-4-yl)-1-piperazinyl]ethyl]-1,2-dihydro-1-quinolineacetamide, 6-chloro-1-methyl-4-[2-[4-(thieno[3,2-c]pyridin-4-yl)-1-piperazinyl]ethyl]-2(1H)-quinolone, 6-chloro-4-[2-[4-(4-fluorobenzoyl)-1-piperidyl]ethyl]-1-methyl-2(1H)-quinolone, 7-fluoro-4-[2-[4-(thieno[3,2-c]pyridin-4-yl)-1-piperazinyl]ethyl]-2(1H)-quinolone, 4-[2-[4-(4-fluorobenzoyl)-1-piperidyl]ethyl]-6-methoxy-2(1H)-quinolone, 6-hydroxy-1-methyl-4-[2-[4-(thieno[3,2-c]pyridin-4-yl)-1-piperazinyl]ethyl]-2(1H)-quinolone, 2-[7-fluoro-2-oxo-4-[2-[4-(thieno[3,2-c]pyridin-4-yl)-1-piperazinyl]ethyl]-1,2-dihydro-1-quinolinyl]ethyl acetate and, 6-methyl-4-[2-[4-(thieno[3,2-c]pyridin-4-yl)-1-piperazinyl]ethyl]-2(1H)-quinolone as well as their addition salts with pharmaceutically acceptable acids or bases.

7. Process for preparing a compound of formula (Ib)

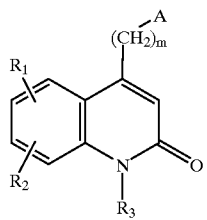

(Ib)

in which

A represents either a 4-(thieno[3,2-c]pyridin-4-yl)-1-piperazinyl group or a 4-(4-fluorobenzoyl)-1-piperidyl group, $R_1$ and $R_2$ each represent, independently of one another, a hydrogen atom, a halogen atom, an amino group, an hydroxyl group, a nitro group, a cyano group, a $(C_1-C_6)$alkyl group, a $C_1-C_6$ alkoxy group, a trifluoromethyl group, a trifluoromethoxy group, a —COOH group, a group —COOR$_4$, a —CONH$_2$ group, a group —CONHR$_4$, a group —CONR$_4$R$_5$, a group —SR$_4$, a group —SO$_2$R$_4$, a group —NHCOR$_4$, a group —NHSO$_2$R$_4$, or a group —N(R$_4$)$_2$, where R$_4$ and R$_5$ are each a $(C_1-C_4)$alkyl group, and m is equal to 2, 3 or 4, and R$_3$ is other than a hydrogen atom, comprising reacting a compound of formula (Ia)

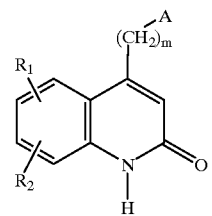

(Ia)

is reached with an electrophilic agent.

8. Process for preparing a compound according to claim 1, comprising reacting 4-(1-piperazinyl)thieno[3,2-c]pyridine or 4-(4-fluorobenzoyl)piperidine with a compound of formula (VII)

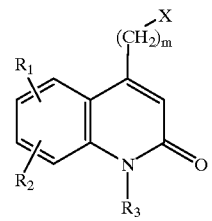

(VII)

in which $R_1$ and $R_2$ each represent, independently of one another, a hydrogen atom, a halogen atom, an amino group, an hydroxyl group, a nitro group, a cyano group, a $(C_1-C_6)$ alkyl group, a $(C_1-C6)$alkoxy group, a trifluoromethyl group, a trifluoromethoxy group, a —COOH group, a group —COOR$_4$, a —CONH$_2$ group, a group —CONHR$_4$, a group —CONR$_4$R$_5$, a group —SR$_4$, a group —SO$_2$R$_4$, a group —NHCOR$_4$, a group —NHSO$_2$R$_4$, or a group —N(R$_4$)$_2$, where R$_4$ and R$_5$ are each a $(C_1-C_4)$alkyl group, R$_3$ represents a hydrogen atom, a $(C_1-C_4)$alkyl group, a group —(CH$_2$)$_p$OH, a group —(CH$_2$)$_p$NH$_2$, a group —(CH$_2$)$_n$COOH, a group —(CH$_2$)$_n$COOR$_4$, a group —(CH$_2$)$_n$CONH$_2$, a group —(CH$_2$)$_n$CONHOH, a group —(CH$_2$)$_p$SH, a group —(CH$_2$)$_n$SO$_3$H, a group —(CH$_2$)$_n$SO$_2$NH$_2$, a group —(CH$_2$)$_n$SO$_2$NHR$_4$, a group —(CH$_2$)$_n$SO$_2$NR$_4$R$_5$, a group —(CH$_2$)$_n$CONHR$_4$, a group —(CH$_2$)$_n$CONR$_4$R$_5$, a group —(CH$_2$)$_p$NHSO$_2$R$_4$, a group —(CH$_2$)$_p$NHCOR$_4$, or a group —(CH$_2$)$_p$OCOR$_4$, where R$_4$ and R$_5$ are each a $(C_1-C_4)$alkyl group, n is equal to 1, 2, 3 or 4, p is equal to 2, 3 or 4 and m is equal to 2, 3 or 4, and X represents a leaving group.

9. Pharmaceutical composition, comprising a compound according to claim 1, in combination with a pharmaceutically acceptable excipient.

* * * * *